(12) United States Patent
Connor

(10) Patent No.: US 8,276,588 B1
(45) Date of Patent: *Oct. 2, 2012

(54) RESPIRATORY MASK WITH ADJUSTABLE SHAPE

(75) Inventor: Robert A. Connor, Minneapolis, MN (US)

(73) Assignee: Sleepnea, Forest Lake, MN (US)

( * ) Notice: Subject to any disclaimer, the term of this patent is extended or adjusted under 35 U.S.C. 154(b) by 405 days.

This patent is subject to a terminal disclaimer.

(21) Appl. No.: 12/589,405

(22) Filed: Oct. 23, 2009

(51) Int. Cl.
*A62B 18/02* (2006.01)
*A62B 18/08* (2006.01)

(52) U.S. Cl. ......... 128/206.24; 128/206.26; 128/206.21; 128/205.25

(58) Field of Classification Search ............. 128/205.25, 128/206.12, 206.16, 206.21, 206.24, 206.26; 2/173, 411–420
See application file for complete search history.

(56) References Cited

U.S. PATENT DOCUMENTS

| | | | |
|---|---|---|---|
| 3,330,274 A | 7/1967 | Bennett | |
| 3,982,532 A | 9/1976 | Halldin et al. | |
| 4,069,516 A | 1/1978 | Watkins, Jr. | |
| 4,657,010 A | 4/1987 | Wright | |
| 4,907,584 A | 3/1990 | McGinnis | |
| 4,915,106 A | 4/1990 | Aulgur et al. | |
| 4,971,051 A | 11/1990 | Toffolon | |
| 5,074,297 A | 12/1991 | Venegas | |
| 5,243,971 A | 9/1993 | Sullivan et al. | |
| 5,465,712 A | 11/1995 | Malis et al. | |
| 5,492,116 A | 2/1996 | Scarberry et al. | |
| 5,503,147 A | 4/1996 | Bertheau | |
| 5,540,223 A | 7/1996 | Starr et al. | |
| 5,560,354 A | 10/1996 | Berthon-Jones et al. | |
| 5,570,689 A | 11/1996 | Starr et al. | |
| 5,623,923 A * | 4/1997 | Bertheau et al. | ......... 128/207.11 |
| 5,647,357 A | 7/1997 | Barnett et al. | |
| 5,655,527 A | 8/1997 | Scarberry et al. | |
| 5,662,101 A | 9/1997 | Ogden et al. | |
| 5,673,690 A | 10/1997 | Tayebi et al. | |
| 5,699,791 A | 12/1997 | Sukiennik et al. | |
| 5,746,201 A | 5/1998 | Kidd | |
| 5,832,918 A | 11/1998 | Pantino | |
| 5,884,624 A | 3/1999 | Barnett et al. | |
| 5,887,587 A | 3/1999 | Groenke | |
| 5,921,239 A | 7/1999 | McCall et al. | |
| 6,019,101 A | 2/2000 | Cotner et al. | |
| 6,112,746 A | 9/2000 | Kwok et al. | |
| 6,192,886 B1 | 2/2001 | Rudolph | |
| 6,196,223 B1 | 3/2001 | Belfer et al. | |
| 6,341,606 B1 | 1/2002 | Bordewick et al. | |
| 6,357,441 B1 | 3/2002 | Kwok et al. | |
| 6,397,847 B1 | 6/2002 | Scarberry et al. | |
| 6,412,488 B1 | 7/2002 | Barnett et al. | |
| 6,418,928 B1 | 7/2002 | Bordewick et al. | |
| 6,425,395 B1 | 7/2002 | Brewer et al. | |
| 6,464,924 B1 | 10/2002 | Thornton | |

(Continued)

*Primary Examiner* — Justine Yu
*Assistant Examiner* — Valerie L Skorupa

(57) ABSTRACT

This invention is a respiratory mask for delivering pressurized gas with a perimeter that can be custom fitted to the contours of a person's face by active and individual adjustment of multiple shape-changing members in the body of the mask. In different embodiments of this invention, the shape-changing members may be located around the perimeter of the mask and individually adjusted by inflation, other pneumatic means, hydraulic means, electric means, or magnetic means. The resulting mask can conform to the contours of an individual's face, even while they sleep, so that there are no places around the mask that fit too tightly (causing irritation, skin marks, and pain) and no places that fit too loosely (causing air leaks).

10 Claims, 2 Drawing Sheets

U.S. PATENT DOCUMENTS

| | | |
|---|---|---|
| 6,467,483 B1 | 10/2002 | Kopacko et al. |
| 6,513,526 B2 | 2/2003 | Kwok et al. |
| 6,530,373 B1 | 3/2003 | Patron et al. |
| 6,581,602 B2 | 6/2003 | Kwok et al. |
| 6,615,834 B2 | 9/2003 | Gradon et al. |
| 6,631,718 B1 | 10/2003 | Lovell |
| 6,634,358 B2 | 10/2003 | Kwok et al. |
| 6,651,663 B2 | 11/2003 | Barnett et al. |
| 6,701,926 B2 | 3/2004 | Olsen et al. |
| 6,728,589 B1 | 4/2004 | Delache et al. |
| 6,729,333 B2 | 5/2004 | Barnett et al. |
| 6,772,760 B2 | 8/2004 | Frater et al. |
| 6,789,541 B2 | 9/2004 | Olsen et al. |
| 6,843,249 B2 | 1/2005 | Bergamaschi et al. |
| 6,851,428 B2 | 2/2005 | Dennis |
| 6,854,465 B2 | 2/2005 | Bordewick et al. |
| 6,857,428 B2 | 2/2005 | Thornton |
| 6,886,564 B2 | 5/2005 | Sullivan et al. |
| 6,895,965 B2 | 5/2005 | Scarberry et al. |
| 6,951,218 B2 | 10/2005 | Gradon et al. |
| 6,959,710 B2 | 11/2005 | Barnett et al. |
| 6,981,502 B2 | 1/2006 | McCormick et al. |
| 6,986,352 B2 | 1/2006 | Frater et al. |
| 7,007,696 B2 | 3/2006 | Palkon et al. |
| 7,021,311 B2 | 4/2006 | Gunaratnam et al. |
| 7,021,312 B2 | 4/2006 | Cannon |
| 7,044,130 B2 | 5/2006 | Jones, Jr. et al. |
| 7,069,933 B2 | 7/2006 | Kwok et al. |
| 7,107,989 B2 | 9/2006 | Frater et al. |
| 7,121,279 B2 | 10/2006 | Dennis |
| 7,171,966 B2 | 2/2007 | Schrader et al. |
| 7,178,527 B2 | 2/2007 | Kwok et al. |
| 7,219,670 B2 | 5/2007 | Jones, Jr. et al. |
| 7,237,551 B2 | 7/2007 | Ho et al. |
| 7,243,650 B2 | 7/2007 | Thornton |
| 7,243,651 B2 | 7/2007 | Kwok et al. |
| 7,273,052 B2 | 9/2007 | Gossweiler |
| 7,287,528 B2 | 10/2007 | Ho et al. |
| 7,308,895 B2 | 12/2007 | Wixey et al. |
| 7,318,439 B2 | 1/2008 | Raje et al. |
| 7,320,323 B2 | 1/2008 | Lang et al. |
| 7,353,827 B2 | 4/2008 | Geist |
| 7,455,063 B2 | 11/2008 | Geiselhart et al. |
| 7,472,703 B2 | 1/2009 | Hernandez et al. |
| 7,481,221 B2 | 1/2009 | Kullik et al. |
| 7,503,327 B2 | 3/2009 | Gunaratnam |
| 7,523,754 B2 | 4/2009 | Lithgow et al. |
| 7,546,837 B2 | 6/2009 | Busch et al. |
| 2004/0118406 A1* | 6/2004 | Lithgow et al. ........... 128/206.24 |
| 2005/0092327 A1* | 5/2005 | Fini et al. ................. 128/206.26 |
| 2005/0199240 A1 | 9/2005 | Hall |
| 2006/0027236 A1 | 2/2006 | Barnett et al. |
| 2006/0027237 A1 | 2/2006 | Sleeper et al. |
| 2006/0032504 A1 | 2/2006 | Burton et al. |
| 2006/0118117 A1 | 6/2006 | Berthon-Jones et al. |
| 2006/0185675 A1* | 8/2006 | Colin ....................... 128/206.24 |
| 2006/0283456 A1 | 12/2006 | Geiselhart et al. |
| 2008/0035152 A1 | 2/2008 | Ho et al. |
| 2008/0053446 A1 | 3/2008 | Sleeper et al. |
| 2008/0060653 A1 | 3/2008 | Hallett et al. |
| 2008/0230068 A1 | 9/2008 | Rudolph |
| 2009/0078267 A1 | 3/2009 | Burz et al. |
| 2009/0095301 A1 | 4/2009 | Hitchcock et al. |
| 2009/0107506 A1 | 4/2009 | Collazo et al. |
| 2009/0159084 A1 | 6/2009 | Sher et al. |

* cited by examiner

RESPIRATORY MASK WITH ADJUSTABLE SHAPE

CROSS-REFERENCE TO RELATED APPLICATIONS

Not Applicable

FEDERALLY SPONSORED RESEARCH

Not Applicable

SEQUENCE LISTING OR PROGRAM

Not Applicable

BACKGROUND

1. Field of Invention

This invention relates to masks that assist respiration.

2. Background

Obstructive Sleep Apnea (OSA) is intermittent blockage of a person's airflow while they sleep due to movement of their tongue or other soft tissue. Such blockages can happen hundreds of times each night, causing poor sleep and oxygen deprivation. Basically, the person temporarily stops breathing during each blockage. Unfortunately, the person might not even be aware of this serious problem because they never fully wake up during blockages.

Obstructive sleep apnea can cause serious long-term harmful effects. These harmful effects include: disrupted sleep; chronic fatigue; morning headaches; irritability; brain damage; cognitive dysfunction; impotency; high blood pressure; heart attacks; congestive heart failure; motor vehicle crashes; job-site accidents; and even death. Despite these harmful effects, it is estimated that only 5% to 8% of the affected population are treated. Approximately 20 million Americans and 35 million people worldwide have obstructive sleep apnea and the number is growing rapidly.

The first-line therapy for most people who are diagnosed with obstructive sleep apnea is Continuous Positive Airway Pressure (CPAP). CPAP keeps the airway open with a stream of pressurized air that is channeled into a person's nose (or nose and mouth) while they sleep. The positive pressure keeps their tongue and other soft tissue from blocking the airway. A CPAP machine continuously pumps pressurized air into a CPAP mask that fits over a person's face while they sleep. Some CPAP masks cover only the sleeper's nose. Other CPAP masks cover both the sleeper's nose and mouth.

In many respects, the mask is the weak link of CPAP. CPAP only works if a person tolerates wearing the CPAP mask and if the mask does not leak pressurized air. If the mask fits too tightly in some places where the mask presses against the person's face, then this can cause skin irritation, red marks, and pain. These problems contribute to high non-compliance with CPAP therapy; many people are not willing to wear a CPAP mask while they sleep. Estimates of the percentage of people who should wear CPAP masks but do not wear them range as high as 50%. On the other hand, if the mask fits too loosely and there are gaps in some places between the mask and the person's face, then the mask leaks pressurized air. Air leaks erode the clinical effectiveness of CPAP.

The main challenge for designing a CPAP mask is how to create a mask that closely conforms to the contours of an individual's face while they sleep so that there are no places around the mask that fit too tightly (causing irritation, skin marks, and pain) and no places that fit too loosely (causing air leaks). This challenge is especially difficult because different people can have quite different facial contours. Also, facial tissue contours can change during sleep. For example, facial contours can shift as a person rests their head and face on a pillow, particularly for people who sleep on their side or on their stomach. The ideal CPAP mask should not only be adjustable to custom fit the contours of an individual's face, but should also adjust to changes in that person's facial contours while the person sleeps.

There are various approaches in the prior art that attempt to address this main challenge for CPAP design. These approaches include: masks with adjustable straps; masks whose overall size can be manually adjusted; masks with a cushion seal filled with a gas, liquid, or gel; masks with an inflatable single-compartment cushion seal; masks that are custom fitted for a person's face by pressing moldable material against their face; and masks that are custom fitted for a person's face using three-dimensional facial imaging and custom fabrication. Some prior art combines two or more of these approaches. For example, one can design a mask with both adjustable straps and a gel cushion.

However, none of the approaches in the prior art have solved the main challenge of how to create a CPAP mask that conforms and adapts to the contours of an individual's face while they are wearing the mask. Accordingly, skin irritation from tight places around CPAP mask perimeters and air leaks from loose places around CPAP mask perimeters remain ongoing problems in CPAP therapy. There is still a clinical need for an innovative CPAP mask to correct these problems. This need is met by the invention disclosed herein. This invention can custom fit a CPAP mask to the contours of particular individual's face while the person is wearing the mask, even while they sleep. This invention can achieve uniform pressure on the person's face around the entire perimeter of the mask to reduce skin irritation and air leaks. This can increase patient compliance with CPAP therapy and reduce obstructive sleep apnea's harmful effects.

We now review the five general approaches that have been pursued in the prior art to address these CPAP mask problems and discuss the limitations of each approach. Then we introduce the invention disclosed herein and discuss how it addresses the limitations of these approaches in the prior art.

REVIEW OF RELATED ART

1. Manually-Adjustable Mask Straps

One of the most common approaches to fitting a CPAP mask to a person's face is to use adjustable straps or other adjustable means by which the main body of the mask is attached to a person's head. By manually tightening or loosening these straps, a person can adjust the overall pressure and the overall angle of the main body of the mask that presses against their face. Such gross adjustments of overall mask pressure and angle can correct large-scale air leakage and mask tightness, but do not provide localized control of the shape of the mark perimeter to selectively correct smaller-scale air leaks and tight spots. Even if a mask has a compressible or stretchable seal, adjustable straps provide only limited ability to change the actual shape of the mask perimeter in order to fit the specific contours of an individual's face.

For example, a person may have both concave and convex facial features in the same area near an adjustable strap; the person may have a fold in their skin next to the bridge of their nose or a wrinkle in their skin next to a high cheek bone. If this person adjusts the strap to make it loose, then air leaks out through the concave feature of their face. If the person adjusts the strap to make it tight, then the mask pinches the skin on the convex feature of their face. Ideally, the person would like a mask that allows them to expand only the segment of the mask perimeter above the concave feature and to shrink only the segment of the mask above the convex feature. However, adjustable straps do not provide such localized control of the shape of the mask perimeter.

As another limitation, manually-adjustable straps do not enable real-time adjustment of a CPAP mask in response to changes in a person's facial contours while they are sleeping. For example, when a person tosses and turns in their sleep, the soft tissue of their face can be compressed intermittently. This is especially true when a person sleeps on their side or stomach and presses their face against a pillow. This facial compression changes the contours of their face which can create tight spots or air leaks that did not exist when the person manually adjusted the mask straps before going to bed. Manually-adjustable straps do not correct tight spots or air leaks that happen during the night. Ideally, one would like a CPAP mask that could automatically adjust perimeter shape to correct tightness or air leaks in real time.

There are a large number of examples of CPAP masks in the prior art that use manually-adjustable straps to fit the main body of the mask to a person's face. Some of the most innovative examples include: U.S. Pat. Nos. 4,915,106 (Aulgur et al., 1990), 5,503,147 (Bertheau, 1996), and 6,886,564 (Sullivan et al., 2005), and U.S. Patent Application 20060032504 (Burton et al., 2006).

2. Compressible Seal or Single-Compartment Inflatable Seal

Another approach to fitting a CPAP mask to an individual's face is to use a compressible seal or a single-compartment inflatable seal between the mask perimeter and the person's face. Compressible seals are intended to passively conform to the contours of a person's face when they are pressed against a person's face. Single-compartment inflatable seals supplement passive compression from contact with a person's face with active expansion by inflation of a cushion seal. Compressible seals may be flexible hollow structures, structures filled with compressible foam, or cushions filled with air, liquid, or gel. Single-compartment inflatable seals may be cushions inflated with air, liquid, or gel. Either type of seal may be used in combination with adjustable straps.

Compressible or single-compartment inflatable seals provide some degree of mask perimeter flexibility to conform to the contours of an individual's face. Single-compartment inflatable seals offer greater control for adjusting overall pressure between the mask and face than do seals based on compression alone. However, like adjustable straps, compressible or single-compartment inflatable seals do not provide localized control of the shape of the mark perimeter to selectively correct smaller-scale air leaks and tight spots.

For example, suppose that there is an air leak at one location of the mask perimeter because of a gap between the mask and the person's face due to a crease in the person's facial tissue. The rest of the mask fits snugly and comfortably. With a single-component inflatable seal, one may be able to inflate the cushion seal sufficiently to eliminate the gap and air leak, but this can make the rest of the mask uncomfortable tight. With uniform inflation of a single component seal, there is no way to target expansion or contraction of certain places along the mask perimeter in order to precisely match an individual's facial contours.

Examples of CPAP masks in the prior art that appear to use a compressible seal or a single-compartment inflatable seal include the following U.S. Pat. Nos. 3,330,274 (Bennett, 1967), 3,982,532 (Halldin et al., 1976), 4,069,516 (Watkins Jr., 1978), 4,907,584 (McGinnis, 1990), 4,971,051 (Toffolon, 1990), 5,074,297 (Venegas, 1991), 5,243,971 (Sullivan et al., 1993), 5,465,712 (Malis et al., 1995), 5,492,116 (Scarberry et al., 1996), 5,540,223 (Starr et al., 1996), 5,560,354 (Berthon-Jones et al., 1996), 5,647,357 (Barnett et al., 1997), 5,655,527 (Scarberry et al., 1997), 5,662,101 (Ogden et al., 1997), 5,699,791 (Sukiennik et al., 1997), 5,746,201 (Kidd, 1998), 5,884,624 (Barnett et al., 1999), 5,887,587 (Groenke, 1999), 6,019,101 (Cotner et al., 2000), 6,112,746 (Kwok et al., 2000), 6,196,223 (Belfer et al., 2001), 6,341,606 (Bordewick et al., 2002), 6,357,441 (Kwok et al., 2002), 6,397,847 (Scarberry et al., 2002), 6,412,488 (Barnett et al., 2002), 6,418,928 (Bordewick et al., 2002), 6,425,395 (Brewer et al., 2002), 6,467,483 (Kopacko et al., 2002), 6,513,526 (Kwok et al., 2003), and 6,530,373 (Patron et al., 2003).

The list of examples of CPAP masks in the prior art that appear to use a compressible seal or a single-compartment inflatable seal continues with the following U.S. Pat. Nos. 6,581,602 (Kwok et al., 2003), 6,615,834 (Gradon et al., 2003), 6,631,718 (Lovell, 2003), 6,634,358 (Kwok et al., 2003), 6,651,663 (Barnett et al., 2003), 6,701,926 (Olsen et al., 2004), 6,729,333 (Barnett et al., 2004), 6,772,760 (Frater et al., 2004), 6,789,541 (Olsen et al., 2004), 6,854,465 (Bordewick et al., 2005), 6,895,965 (Scarberry et al., 2005), 6,951,218 (Gradon et al., 2005), 6,959,710 (Barnett et al., 2005), 6,981,502 (McCormick et al., 2006), 6,986,352 (Frater et al., 2006), 7,007,696 (Palkon et al., 2006), 7,021,311 (Gunaratnam et al., 2006), 7,021,312 (Cannon, 2006), 7,044,130 (Jones Jr. et al., 2006), 7,069,933 (Kwok et al., 2006), 7,107,989 (Frater et al., 2006), 7,171,966 (Schrader et al., 2007), 7,178,527 (Kwok et al., 2007), 7,219,670 (Jones, Jr. et al., 2007), 7,237,551 (Ho et al., 2007), 7,243,651 (Kwok et al., 2007), 7,273,052 (Gossweiler, 2007), 7,287,528 (Ho et al., 2007), 7,308,895 (Wixey et al., 2007), 7,318,439 (Raje et al., 2008), 7,320,323 (Lang et al., 2008), 7,353,827 (Geist, 2008), 7,455,063 (Geiselhart et al., 2008), 7,472,703 (Hernandez et al., 2009), 7,481,221 (Kullik et al., 2009), 7,503,327 (Gunaratnam, 2009), 7,523,754 (Lithgow et al., 2009), and 7,546,837 (Busch et al., 2009).

The list of examples of CPAP masks in the prior art that appear to use a compressible seal or a single-compartment inflatable seal continues with the following U.S. Patent Applications: 20050199240 (Hall, Matthew, 2005), 20060027236 (Barnett et al., 2006), 20060027237 (Sleeper et al., 2006), 20060283456 (Geiselhart et al., 2006), 20080035152 (Ho et al., 2008), 20080053446 (Sleeper et al., 2008), 20080060653 (Hallett et al., 2008), 20080230068 (Rudolph, 2008), 20090078267 (Burz et al., 2009), 20090095301 (Hitchcock et al., 2009), 20090107506 (Collazo et al., 2009), and 20090159084 (Sher et al., 2009).

3. Manually-Adjustable Overall Mask Size

Another approach to fitting a CPAP mask to an individual's face involves manual adjustment of the overall mask size. Manual adjustment of overall mask size can be done using Velcro straps, sliding snaps, accordion-like folds, vertically-adjustable spacers, or similar methods. Changing overall mask size is very useful for making a "one-size-fits-all" mask that can be adjusted for either adult or pediatric use.

However, the ability to change overall mask size provides only limited ability to change the shape of the mask perimeter to custom fit the contours of an individual's face. There is a lot more variation in facial contours between people other than vertical or horizontal dimensions. Also, the manual aspect of these adjustments does not enable adjustment of the mask in response to facial contour changes while a person sleeps. Accordingly, while masks with manual adjustments of over-all mask size are useful for reducing the need to stock different size masks, they do not eliminate tight spots and leaks due to different facial contours.

Examples of CPAP masks in the prior art that appear to offer manual adjustment of overall mask size include the following: U.S. Pat. Nos. 4,657,010 (Wright, 1987), 5,570,689 (Starr et al., 1996), 5,673,690 (Tayebi et al., 1997), 5,921,239 (McCall et al., 1999), 6,192,886 (Rudolph, 2001), 6,851,428 (Dennis, 2005), and 7,121,279 (Dennis, 2006), and U.S. Patent Application 20060118117 (Berthon-Jones et al., 2006).

4. Customized One-Time Molding Process

Another approach to fitting a CPAP mask to a person's face is by using a one-time molding process with a soft material that hardens. For example, this process can involve: pressing a moldable material, when it is soft, against a person's face so that it matches the contours of the person's face; removing the material from the person's face; allowing the material to harden; and using the material, directly or indirectly, to create a customized mask that exactly fits the contours of that person's face. Unlike the above approaches, this approach can change the shape of the mask perimeter to fit the individual contours of a person's face. However, even this approach has limitations.

One limitation of approach is that a one-time molding process does not provide adjustments for how the mask fits when it is actually being worn. For example, when the mask is actually being worn, it may press against the person's face with a different pressure level, or at a different angle, than the manner in which the moldable material is pressed against the person's face. As another example, a person's facial contours may change due to short-term changes in retention of body fluids or longer-term changes in body weight. As another example, a person's facial contours may change during the night as their face comes into contact with a pillow. Ideally, one would want a CPAP mask whose shape can be continually adjusted to a person's changing facial contours while the person wears the mask, even while they sleep.

Other limitations of the one-time molding approach relate to the expense and inconvenience of the custom molding process. For example, it is unlikely that a person could self-administer the custom molding process. Thus they likely require assistance by another person, such as a health care professional, which can make the whole process expensive and time-consuming. Further, the molding process may involve: exposing the person's skin or lungs to chemicals in the moldable material; the delay of waiting for the moldable substance to harden; and unintended changes in the shape of the mask between when it is removed from the person's face and when it hardens. Ideally, one would want a CPAP mask that easily and continuously adjusts to a person's facial contours, without the involvement and expense of another person.

Examples of CPAP masks in the prior art that appear to use one-time moldable material include the following: U.S. Pat. Nos. 5,832,918 (Pantino, 1998), 6,397,847 (Scarberry et al., 2002), 6,464,924 (Thornton, 2002), 6,843,249 (Bergamaschi et al., 2005), 6,857,428 (Thornton, 2005), 6,895,965 (Scarberry et al., 2005), and 7,243,650 (Thornton, 2007).

5. Customized Fabrication Using 3D Imaging

Another approach to fitting a CPAP mask to a person's face is by using three-dimensional medical imaging and custom fabrication of a mask based on the results of that imaging. In some respects, this is a virtual variation on the one-time molding process, one in which the molding process is done digitally rather than physically. Accordingly, fabrication by 3D imaging has advantages and limitations that are similar to those of a one-time molding process.

Limitations of this approach include: differences in facial contours when a mask is pressed against one's face vs. facial contours during imaging without anything pressed against one's face; changes in facial contours during sleep; and the time and expense involved in 3D medical imaging and custom fabrication. Custom fabrication using 3D imaging is less common than the four approaches described above, but an example of prior art that appears to use custom fabrication using 3D imaging is U.S. Pat. No. 6,728,589 (Delache et al., 2004).

SUMMARY AND ADVANTAGES OF THIS INVENTION

This invention is a mask for delivering a pressurized breathable gas into a person's nose, mouth, or both with a shape that can be adjusted to fit the contours of the person's face. It includes at least two shape-changing members wherein the shapes of two or more shape-changing members can be actively and individually adjusted. Changes in the shapes of the shape-changing members change the shape of the mask perimeter so that the mask better fits the contours of the person's face while the person wears the mask. In different embodiments of this invention, the shape-changing members: are located around the perimeter of the mask that contacts the person's face; and are individually adjusted by inflation, other pneumatic means, hydraulic means, electric means, or magnetic means.

This invention has significant advantages over CPAP masks in the prior art—

Compared to masks with manually-adjustable mask straps, this invention: provides localized control of the shape of the mask perimeter to selectively correct smaller-scale air leaks and tight spots; and allows real-time adjustment of a CPAP mask in response to changes in a person's facial contours while they are sleeping.

Compared to masks with a compressible seal or single-compartment inflatable seal, this invention provides localized control of the shape of the mask perimeter to selectively correct smaller-scale air leaks and tight spots.

Compared to masks with manually-adjustable overall mask size, this invention: provides localized control of the shape of the mask perimeter to selectively correct smaller-scale air leaks and tight spots; and allows real-time adjustment of a CPAP mask in response to changes in a person's facial contours while they are sleeping.

Compared to masks created by a customized one-time molding process, this invention: can adjust to a person's changing facial contours while the person wears the mask, even while they sleep; and self-adjusts without requiring the time and expense of a health care professional.

Compared to masks created by customized fabrication using 3D imaging, this invention: can adjust to a person's changing facial contours while the person wears the mask, even while they sleep; and self-adjusts without requiring the time and expense of 3D medical imaging.

To summarize, the actively and individually adjustable shape-changing members disclosed in this invention create an innovative CPAP mask that conforms to the contours of an individual's face, even while they sleep, so that there are no places around the mask that fit too tightly (causing irritation, skin marks, and pain) and no places that fit too loosely (causing air leaks). This fills an important clinical need that has not been met by CPAP masks in the prior art.

INTRODUCTION TO THE FIGURES

These figures show some possible embodiments of this invention, but do not limit the full generalizability of the claims.

DETAILED DESCRIPTION OF THE FIGURES

These figures show different examples of how this invention may be embodied. However, these examples are not exhaustive. These figures do not limit the full generalizability of the claims.

Figure 1:
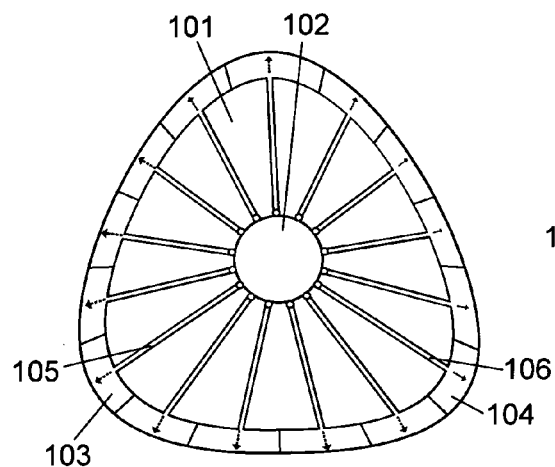
FIG. 1 shows a frontal perspective of an embodiment of this invention with separably inflatable and adjustable members around the mask perimeter.

FIG. 1 shows a frontal perspective of one embodiment of this invention wherein the main body of the mask, 101, has a perimeter that is shaped like a rounded triangle in order to cover a person's nose and mouth. In another example, such as for a person who keeps their mouth closed while they sleep, the mask could be shaped differently to cover only the person's nose. If this mask were placed on a person's face, then the perspective shown in FIG. 1 would be that of looking at the mask while facing the person. There are many different means, including various straps, in the prior art by which the main body of a mask can be attached to a person's head. The precise attachment method is not central to this invention, so the attachment means is not shown here.

In the center of the mask body shown in FIG. 1, there is a circular cross-section of a central tube 102 through which pressurized breathable gas enters the mask to be directed into the person's nose and mouth. Central tube 102 may be made from material selected from the group consisting of ethylene propylene diene monomer, latex, silicone, polyvinyl chloride, and polyurethane. There are many means in the prior art for pressurizing air and for directing it into tubes and the precise mechanism for supplying the pressurized air is not central to this invention. Accordingly, the source of the pressurized air, located at the other end of central tube 102, is not shown here.

FIG. 1 also shows a number of smaller tubes including 105 and 106 that come into the mask around the perimeter of central tube 106 and then bend outwards towards the perimeter of the mask like radial spokes. In this embodiment, these smaller tubes including 105 and 106 conduct a pressurized flowable substance (such as a gas or liquid) into a series of contiguous, but separably inflatable and adjustable members including 103 and 104. These separably inflatable and adjustable members may be made from material selected from the group consisting of latex, nylon, polyethylene terephthalate, and polyvinyl chloride.

The separably inflatable and adjustable members including 103 and 104 are linked together to form the perimeter of the mask that contacts the person's face. The ability to separately adjust the size of each of these inflatable members by individually adjusting the pressure of the flowable substance within each member allows customization of the shape of the perimeter of the mask to make it precisely fit the contours of the person's face, while the mask is being worn.

In this embodiment, the separably inflatable and adjustable members including 103 and 104 are filled with pressurized air. In another example, these members may be filled with a non-toxic liquid or gel. In this embodiment, the pressurized air to inflate these members travels toward the main body of the mask through smaller tubes 105 and 106 which are distributed around the circumference of central tube 102 and connect to a proximal end of the main body of the mask. When these tubes reach the proximal end of the main body of the mask, they then bend outward in a radial manner toward the perimeter, like spokes, and connect with the individual inflatable members including 103 and 104 at a distal end of the main body of the mask. In another example, these smaller tubes could enter the mask in a bundle separate from central tube 102. There are different means of controlling the pressures of flowable substances in tubes in the prior art and the precise means of controlling the different pressures with the smaller tubes is not central to this invention, so this means is not shown here.

Figure 2:
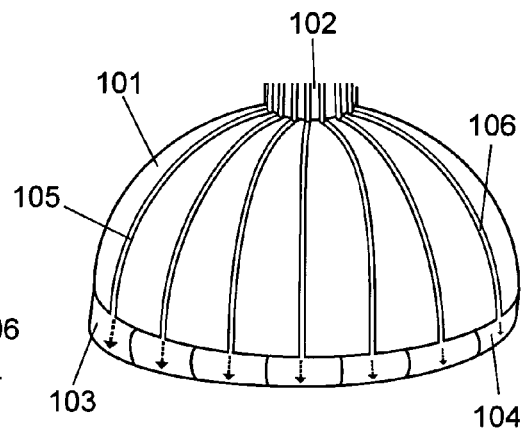
FIG. 2 shows a side view of this embodiment.

FIG. 2 shows a side view of the main body of the mask in this embodiment. If the mask were to be placed on a person's face so as to cover their nose and mouth, then FIG. 2 would be a perspective of the mask looking up at the person's face from below their chin. FIG. 2 shows the parts of the mask that were introduced in FIG. 1 including: main body 101 of the mask, central tube 102 conducting the pressurized gas into the mask for direction into the person's nose and mouth, and smaller radial tubes including 105 and 106 that conduct pressurized air to individually inflate and adjustable the separably inflatable members including 103 and 104.

FIG. 2 highlights that there is more pressurized air pumped through small tube 105 into inflatable member 103 than is pumped through small tube 106 into inflatable member 104. This difference is symbolized by: showing a larger arrow representing air flow in inflatable member 103 than in inflatable member 104; and showing inflatable member 103 as being distended further toward the person's face than inflatable member 104.

The ability to separately and differentially inflate individual members around the perimeter of the mask allows customization of the shape of the perimeter to precisely fit the contours of a particular person's face. In this example, the person's face is asymmetric. This asymmetry is matched by greater inflation of member 103 than member 104. As we will discuss further, this allows a better seal than is possible with methods in the related art such as inflation of a single inflatable ring or facial compression of a single gel ring.

Figure 3:
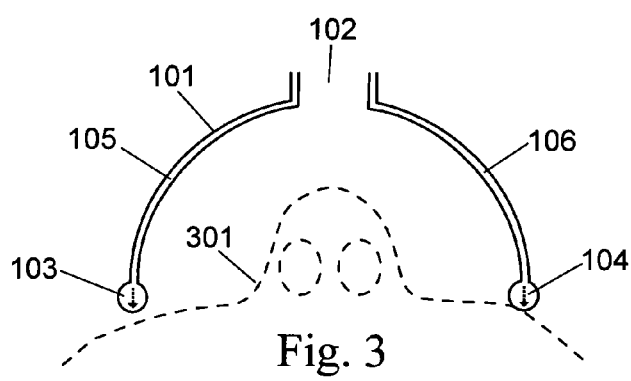
FIG. 3 shows a cross-sectional side view of this embodiment before separate adjustment of the inflatable members.
Figure 4:
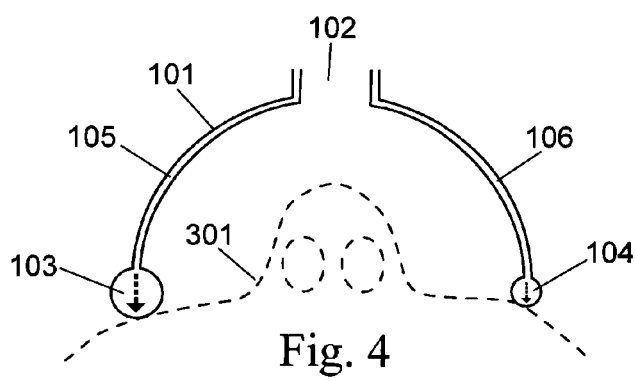
FIG. 4 shows a cross-sectional side view of this embodiment after separate adjustment of the inflatable members.

FIGS. 3 and 4 show a cross-sectional side view of the main body of the mask having been placed on a person's face so as to cover their mouth and nose. With respect to the person's face, this view is from the perspective of looking up at a person's face from below their chin. This is why FIGS. 3 and 4 show the dashed line contours of the person's cheeks and nostrils on the bottom of their nose.

FIG. 3 shows the situation in which the two inflatable members 103 and 104 are inflated equally on a person with an asymmetric face. Equal inflation does not take advantage of the customization by differential pressure adjustment that is possible with this present invention, but is useful for discussion of the limitations of the prior art with a seal made from a single inflatable ring or a single gel-filled ring. We will discuss how equal inflation of two inflatable members is comparable to inflation of single ring in the prior art. FIG. 4 shows the situation in which the two inflatable members 103 and 104 are separably inflated and adjusted with different pressures in order to precisely fit the contours of this person's face. We will discuss how such separate inflation and adjustment is superior to the prior art for avoiding gas leaks, painful tightness, and red marks on the person's face.

In this example, the person's face is asymmetric. The person's cheek profile is lower on the side of the mask under inflatable member 103 than their profile on the side of the mask under inflatable member 104. Body asymmetry is not uncommon. Further, even if a person has a relatively symmetric facial contour during the day, facial contours can change when they lie down with their head against a pillow, especially if they sleep on their side. Also, the same fitting issues apply to not just facial asymmetry, but also to any unique facial contours that are not easily fit by a standardized mask. Although one can adjust the overall angle or pressure of a standardized mask on the face by adjusting the straps that hold it against the face, there are limits to how much straps can change the shape of the mask itself. Accordingly, many people find it difficult to achieve a good seal with a standardized mask. They have to deal with gas leaks in places of too little pressure between the mask and face, painful tightness and red marks in areas of too much pressure between the mask and face, or both problems at different points around the mask perimeter.

FIG. 3 shows the situation in which members 103 and 104 are inflated equally; this does not take advantage of the innovation of this invention and is analogous to a single inflatable ring in the prior art. When the two members 103 and 104 are inflated equally, there is either a gap between the mask and the person's cheek beneath member 103 (as shown in FIG. 3) or a high-pressure spot between the mask and the person's cheek beneath member 104. The gap shown here allows pressurized gas to leak out of the mask. Using a single inflatable ring to form a seal, as done in the prior art, has similar limitations. Masks in the prior art do not offer separably inflatable and adjustable members around the mask perimeter in order to customize the mask perimeter to the contours of a person's face while they are wearing the mask. Accordingly, masks in the prior art with single rings are subject to leaks in a manner similar to that shown with the two members 103 and 104 being equally pressurized.

For masks in the prior art with a single inflatable ring around the entire perimeter of the mask, even if one were to inflate the pressure in that single ring to the level where the single ring touched the surface of the person's face everywhere around the mask perimeter, there would still be adverse differences in pressure between the mask and the person's face in different spots around the mask perimeter. Too little pressure between the mask and face at certain spots around the perimeter causes leaks of pressurized breathable gas, defeating the purpose of the mask. Too much pressure between the mask and face at certain spots around the mask perimeter causes painful tightness and red marks on the skin of the person's face.

These adverse differences in pressure between the mask and the person's face in different spots are caused by the interaction of three forces—one force in one direction and two forces in the opposite direction. In one direction, the pressurized air inside the inflatable ring pushes the elastic membrane of the ring outwards toward the person's face. In the opposite direction, contact with the person's face opposes outward movement of the elastic membrane of the ring by pressurized air and the elasticity of the membrane opposes outward movement of the elastic membrane of the ring by pressurized air.

With a single inflatable ring, one can control the force of the pressurized gas within the ring, but can not control differences in pressure on the face around the mask perimeter. The force of the pressurized gas inside the ring is constant around the perimeter and the inward force of the elastic ring varies depending on how much it is distended, so the amount of pressure between the mask and the face varies around the perimeter of the mask. This adverse variation in facial pressure causes gas leaks, painful tightness, and red creases on the person's face.

Unlike masks in the prior art, with this invention one can control differences in pressure on the face around the mask perimeter. This can eliminate adverse variation in pressure between the mask and face around the mask perimeter. The ability of this present invention to differentially inflate and adjust the pressure of separate inflatable members allows one to create uniform pressure of the mask on the person's face around the perimeter of the mask. This eliminates gas leaks, painful tightness, and red creases on the person's face.

To summarize, being restricted to uniform pressure around the mask perimeter with a single inflatable ring, as in the prior art, results in non-uniform pressure between the mask and the person's face in different places. This causes problems. However, enabling adjustable inflatable members around the mask perimeter, as in this invention, allows uniform pressure between the mask and the person's face in all places. This corrects these problems.

We used FIG. 3 with two, equally-inflated members, as a vehicle to discuss the limitations of masks with a single inflatable ring in the prior art. We now discuss another type of seal in the prior art that has similar limitations. This type of seal comprises a single gel-filled ring that is compressed by contact with a person's face. A single gel-filled ring has problems with pressure differences between the mask and the face that are similar to those of a single inflatable ring.

With a single gel-filled ring, differential extension of the ring at different points around the perimeter of the mask is caused by compression from contact with the person's face at points of maximal contact. Similar to the problems caused by a single inflatable ring, a single gel-filled ring results in spots of greater and lesser pressure between the mask and the face around the mask perimeter. This can result in gas leaks in spots of less pressure and tightness or red marks in spots of greater pressure.

The dynamics of a single gel-filled ring differ from that of a single inflatable ring because the force to push the membrane into conformity with the contour of the person's face comes entirely from compressive force from the person's face, not from an external pressurized flow. In this respect, a gel-filled ring provides even less control for customization than a single inflatable ring because the overall level of pressure against the face can not be adjusted independently from adjustment of mask position. The separably inflatable and adjustable inflatable members of this invention address and correct pressure differentials between the mask and the face in different spots around the perimeter of the mask.

FIG. 4 shows how the separately inflatable and adjustable members around the mark perimeter in this invention, including members 103 and 104, can be individually inflated and adjusted to achieve a customized fit to the contours of this person's face, while the person is wearing the mask. In this example with facial asymmetry, this customization enables the mask to fit the asymmetry, closing the gap that existed under member 103 with equal inflation of members 103 and 104 in FIG. 3. Differential inflation and adjustment of inflatable members 103 versus 104 eliminates the gas leak under member 103 without excessive pressure on the face (and associated pain or red creases on the skin) under member 104.

We have discussed how the ability to separately inflate and adjust members 103 and 104 can reduce leaks from low pressure points around the mask perimeter and pain on the skin from high pressure points around the mask perimeter. This is superior to prior art with a seal from a single inflatable ring or a single gel-filled ring. We now discuss another approach to customizing the fit of a mask to a particular person's face in the prior art and how this invention is superior to that approach.

The prior art includes means of making a customized mask using a one-time face-molding process prior to regular use. The prior art includes the use of moldable materials that change from a relatively soft and moldable state to a relative hard and fixed state. These materials are pressed against a person's face when the materials are in the relatively-soft state so that the materials conform to the contours of that person's face. The materials are then removed from the person's face and harden into a relatively-hard state, keeping a molded contour of that person's face. These materials in their hardened state are then used to create a customized mask directly, by incorporation into a mask, or indirectly, by a second-stage molding process to create materials that are then incorporated into a mask.

This present invention has several advantages over the use of moldable materials to make customized masks in the prior art:

First, this present invention allows real-time adjustment of the contours of the mask while it is being regularly worn. A mask formed from a one-time molding process does not allow real-time adjustments. Such real-time adjustments are especially important when: the pressure of the mask on the face when used regularly changes from the pressure applied in the one-time molding process; the contours of the person's face change from its contours during the one-time molding process, such as when a person sleeps on their side with their face on a pillow or when their weight varies. Further, with this invention, a device could be connected to the mask to monitor the pressure levels of the individual members, to detect gas leakage, and to automatically adjust those individual pressure levels to stop leaks while a person sleeps. This is not possible with a one-time molding process.

Second, this present invention avoids the time and expense of moldable material preparation, pressing, and mask formation in the custom molding process. For example, a person is much more likely to be able to self-adjust the present invention while wearing the mask than to self-apply and remove a moldable mask from their own face. The custom molding process is likely to involve the time and expense of professional assistance in a health care setting, but the present invention can be customized in the person's own home.

Other potential advantages of this present invention over customized masks in the prior art made from a one-time molding process include: avoiding placement of potentially sticky or irritating chemicals in contact with the person's skin; avoiding the delay of waiting for the moldable substance to harden; and avoiding undesirable changes in the shape of the mask between the time it is pressed against the person's face and when it hardens. Undesirable changes in the shape of the mask can occur due to contact of the mask with a support surface if the mask is placed on a support surface or the force of gravity acting on soft material even if the mask is suspended while hardening.

In this embodiment, the separably inflatable and adjustable members including 103 and 104 are in direct contact with the person's face. In another example, there may be a flexible layer between these members and the person's face. In this embodiment, the separably inflatable and adjustable members are contiguous. In another example, these members may be separated by a non-adjustable segment or membrane. In this embodiment, each of the inflatable and adjustable members is individually adjustable. In another example, some but not all of these members may be adjusted in groups. In a variation on this embodiment, one may add pressure sensors to measure the pressure within each of these inflatable members in order to better control pressure differentials among the members.

Figure 5:
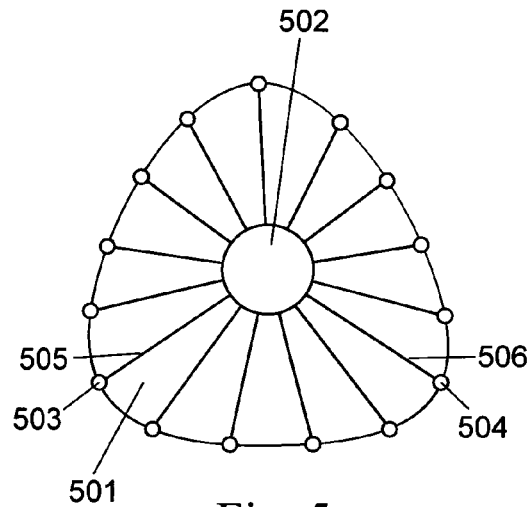
FIG. 5 shows a frontal perspective of an embodiment of this invention with differentially-adjustable cylindrical members around the mask perimeter.

FIGS. 5 through 8 show another embodiment of this invention. In this embodiment, the shape of the mask perimeter is custom fitted to the person's face by differential adjustment of extendable cylindrical members around the mask perimeter. FIG. 5 shows the main body of the mask 501 having a rounded triangular shape in order to cover the person's nose and mouth. Central tube 502 conveys pressurized breathable gas into the mask for direction into the person's nose and mouth.

In the embodiment shown in FIG. 5, radial wires including 505 and 506 convey electricity that powers extendable cylindrical members including members 503 and 504. In this embodiment, the extendable cylindrical members, including 503 and 504, are Micro Electrical Mechanical Systems (MEMS) whose lengths can be adjusted individually. In another example, the extendable cylindrical members, including 503 and 504, could be hydraulic or pneumatic pistons powered by pressurized flows through microtubes. In this latter example, 505 and 506 would be microtubes conducting pressurized flows instead of wires conducting electricity. In all of these examples, the extension or contraction of each of the extendable cylindrical members, including 503 and 504, is individually adjustable to customize the mask perimeter to best fit the person's face.

Figure 6:
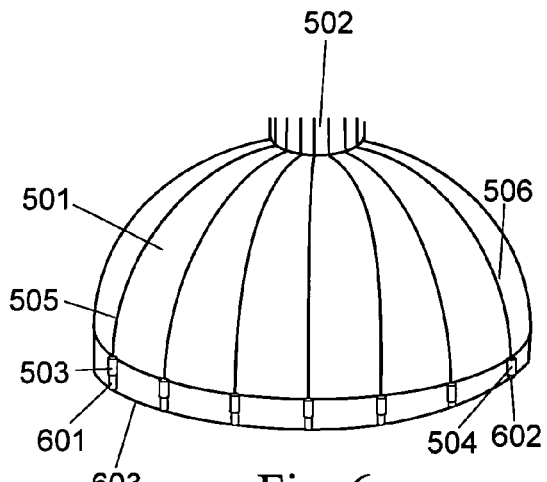
FIG. 6 shows a side view of the embodiment in FIG. 5.

FIG. 6 shows a side view of the embodiment introduced in FIG. 5. In FIG. 6, one can more clearly see the structure of the extendable cylindrical members around the perimeter of the mask. Each of the extendable cylindrical members has an outer hollow cylinder, such as 503 or 504, and a concentric inner cylinder, such as 601 or 602, that slides in or out of the outer cylinder. Extension or contraction of each of the extendable cylindrical members is powered and controlled by a separate wire, such as wire 505 or 506. In this embodiment, the ends of the extendable cylindrical members that point toward the person's face are connected by link segments, including 603, to create a continuous adjustable seal between the mask and the contours of the person's face. In another example, the ends of the extendable cylindrical members may connect to a continuous flexible layer to create a continuous adjustable seal.

Figure 7:
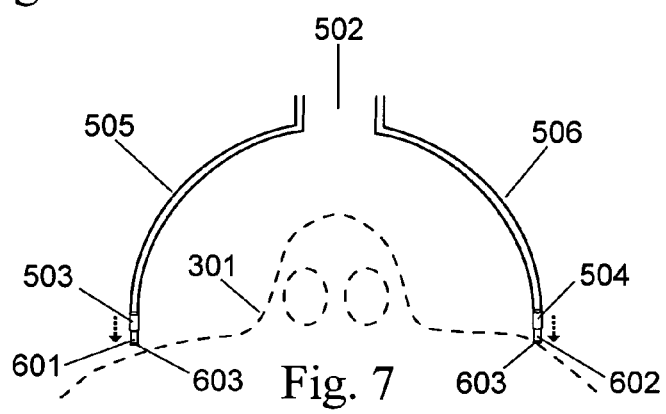
FIG. 7 shows a cross-sectional side view of the embodiment in FIG. 5 before separate adjustment of the cylindrical members.
Figure 8:
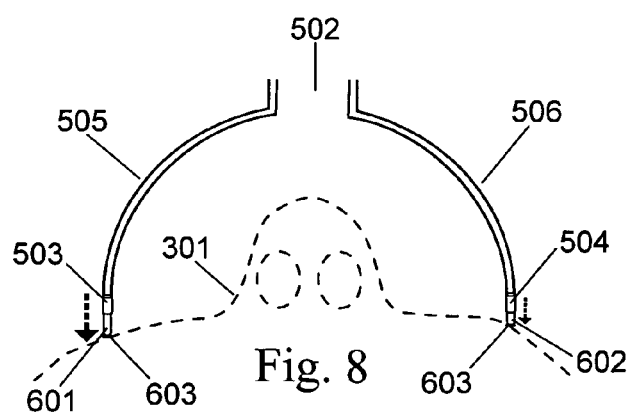
FIG. 8 shows a cross-sectional side view of the embodiment in FIG. 5 after separate adjustment of the cylindrical members.

FIGS. 7 and 8 show how the extendable cylindrical members in this embodiment may be differentially extended in order to custom fit the perimeter of the mask to the contours of a person's face while the person is wearing the mask.

I claim:

1. A mask for delivering a pressurized breathable gas into a person's nose, mouth, or both with a shape that can be adjusted to fit the contours of the person's face, comprising:
   a mask for directing a pressurized breathable gas into a person's nose, mouth, or both that includes at least two shape-changing members;
   wherein these shape-changing members comprise extendable cylindrical members, extendable pistons, or both;
   wherein the shapes of two or more shape-changing members can be actively, individually, reversibly, and automatically adjusted by a means selected from the group consisting of hydraulic pistons, pneumatic pistons, and Micro Electrical Mechanical Systems (MEMS); and wherein changes in the shapes of the shape-changing members change the shape of the mask perimeter so that the mask better fits the contours of the person's face while the person wears the mask.

2. The mask in claim 1 wherein the shape-changing members are located along the perimeter of the mask that is in contact with the person's face.

3. The mask in claim 1 wherein changes in the shapes of the shape-changing members can occur automatically while the person sleeps.

4. The mask in claim 1 wherein adjustment of the shapes of the shape-changing members occurs automatically throughout the night, using feedback from leak sensors and/or pressure sensors, in order to eliminate low-pressure spots that leak gas and high-pressure spots that cause pain or red marks as the person tosses and turns in their sleep.

5. The mask in claim 1 wherein the changes in the shape of the mask perimeter include changes selected from the group consisting of: changes in the distances or pressures between the mask perimeter and the person's face at different locations around the mask perimeter; changes in the contour or curvature of the mask perimeter; and changes in the height, width, or cross-sectional area of the mask perimeter.

6. A mask for delivering a pressurized breathable gas into a person's nose, mouth, or both with a shape that can be adjusted to fit the contours of the person's face, comprising:
   a mask for directing a pressurized breathable gas into a person's nose, mouth, or both that includes at least two shape-changing members along the perimeter of the mask that is in contact with the person's face,
   wherein these shape-changing members comprise extendable cylindrical members, extendable pistons, or both;
   wherein the shapes of two or more shape-changing members can be actively, individually, reversibly, and automatically adjusted by a means selected from the group consisting of hydraulic pistons, pneumatic pistons, and Micro Electrical Mechanical Systems (MEMS),
   wherein changes in the shapes of the shape-changing members change the shape of the mask perimeter, apart from the effects of compression against the person's face, so that the mask better fits the contours of the person's face while the person wears the mask, and
   wherein adjustment of the shapes of the shape-changing members occurs automatically throughout the night, using feedback from leak sensors and/or pressure sensors, in order to eliminate low-pressure spots that leak gas and high-pressure spots that cause pain or red marks as the person tosses and turns in their sleep.

7. The mask in claim 6 wherein the changes in the shape of the mask perimeter include changes selected from the group consisting of: changes in the distances or pressures between the mask perimeter and the person's face at different locations around the mask perimeter; changes in the contour or curvature of the mask perimeter; and changes in the height, width, or cross-sectional area of the mask perimeter.

8. A mask for delivering a pressurized breathable gas into a person's nose, mouth or both with a shape that can be adjusted to fit the contours of the person's face, comprising:
   a main body having a proximal end and a distal end;
   a central tube through which pressurized breathable gas enters the main body;
   two or more small tubes, wherein these tubes are smaller in diameter than the central tube, wherein these tubes travel along the central tube to connect to the proximal end of the main body of the mask, and wherein these tubes span outwards from the perimeter of the central tube after reaching the main body of the mask; and
   two shape-changing members along the perimeter of the mask that is in contact with the person's face; wherein these shape-changing members can be actively, individually, and reversibly adjusted using pressurized gas that travels through the two or more small tubes; and wherein changes in the shapes of the shape-changing members change the shape of the mask perimeter so that the mask better fits the contours of the person's face while the person wears the mask.

9. The mask in claim 8 wherein adjustment of the shapes of the shape-changing members occurs automatically throughout the night, using feedback from leak sensors and/or pressure sensors, in order to eliminate low-pressure spots that leak gas and high-pressure spots that cause pain or red marks as the person tosses and turns in their sleep.

10. The mask in claim 8 wherein the changes in the shape of the mask perimeter include changes selected from the group consisting of: changes in the distances or pressures between the mask perimeter and the person's face at different locations around the mask perimeter; changes in the contour or curvature of the mask perimeter; and changes in the height, width, or cross-sectional area of the mask perimeter.

\* \* \* \* \*